United States Patent
Dees et al.

(10) Patent No.: US 12,048,627 B2
(45) Date of Patent: *Jul. 30, 2024

(54) ANATOMICALLY RELIEVED AUGMENTS

(71) Applicant: Smith & Nephew, Inc., Memphis, TN (US)

(72) Inventors: Roger Ryan Dees, Senatobia, MS (US); Jeffrey N. Yeager, Nesbit, MS (US); Angela Mines, Arlington, TN (US); Paul Charles Crabtree, Nesbit, MS (US)

(73) Assignee: Smith & Nephew, Inc., Memphis, TN (US)

( * ) Notice: Subject to any disclaimer, the term of this patent is extended or adjusted under 35 U.S.C. 154(b) by 486 days.

This patent is subject to a terminal disclaimer.

(21) Appl. No.: 17/399,252

(22) Filed: Aug. 11, 2021

(65) Prior Publication Data
US 2021/0369461 A1    Dec. 2, 2021

Related U.S. Application Data

(63) Continuation of application No. 16/216,437, filed on Dec. 11, 2018, which is a continuation of application
(Continued)

(51) Int. Cl.
*A61F 2/30* (2006.01)

(52) U.S. Cl.
CPC .............. *A61F 2/30734* (2013.01); *A61F 2002/30736* (2013.01); *A61F 2002/30738* (2013.01); *A61F 2220/0025* (2013.01)

(58) Field of Classification Search
CPC ........ A61F 2/30734; A61F 2002/30736; A61F 2002/30738; A61F 2220/0025
See application file for complete search history.

(56) References Cited

U.S. PATENT DOCUMENTS

| 7,291,174 B2 | 11/2007 | German et al. |
| 8,382,849 B2 | 2/2013 | Thomas |

(Continued)

FOREIGN PATENT DOCUMENTS

| CN | 1481766 A | 3/2004 |
| CN | 101351172 A | 1/2009 |

(Continued)

OTHER PUBLICATIONS

Examination Report for Australian Paten Application No. 2016260418, mailed Dec. 19, 2019.
(Continued)

*Primary Examiner* — Ariana Zimbouski
*Assistant Examiner* — Christine L Nelson
(74) *Attorney, Agent, or Firm* — KDW Firm PLLC

(57) ABSTRACT

Anatomically shaped augments that are configured for implantation in a bone and which have one or more reliefs. A distal end of an outer portion of the augment can have a shape that is configured to generally conform to the shape of a metaphyseal-diaphyseal junction of an intramedullary canal of a bone. A proximal end of the outer portion can have a shape that is configured to generally conform to a shape of the metaphyseal region of the intramedullary canal. The reliefs can be configured to reduce a size of the augment and enhance the degree of freedom in the implant positioning and/or sizing of the augment. Further, such reliefs may contour the augment so as to prevent cortical bone contact and/or prevent contact with the implant device that may be associated with misalignment between an intramedullary canal and metaphyseal or diaphyseal regions of the bone.

22 Claims, 6 Drawing Sheets

Related U.S. Application Data

No. 15/572,943, filed as application No. PCT/US2016/032349 on May 13, 2016, now abandoned.

(60) Provisional application No. 62/160,891, filed on May 13, 2015.

(56) References Cited

U.S. PATENT DOCUMENTS

| | | | |
|---|---|---|---|
| 8,424,183 | B2 | 4/2013 | Thomas |
| 9,532,879 | B2 | 1/2017 | Liberman et al. |
| 10,335,284 | B2 | 7/2019 | Landon et al. |
| 11,116,637 | B2 * | 9/2021 | Dees .................. A61F 2/30734 |
| 2004/0049286 | A1 | 3/2004 | German et al. |
| 2004/0162619 | A1 | 8/2004 | Blaylock et al. |
| 2013/0172892 | A1 | 7/2013 | Servidio et al. |
| 2013/0304221 | A1 | 11/2013 | Blaylock et al. |
| 2014/0277528 | A1 | 9/2014 | Mines et al. |
| 2014/0277567 | A1 | 9/2014 | Collazo et al. |

FOREIGN PATENT DOCUMENTS

| | | |
|---|---|---|
| CN | 103690277 A | 4/2014 |
| EP | 1396240 A2 | 3/2004 |
| EP | 2679201 A1 | 1/2014 |
| EP | 2130516 B1 | 3/2014 |
| IN | 103637837 A | 3/2014 |
| JP | 2009-291608 A | 12/2009 |
| JP | 2009-291609 A | 12/2009 |

OTHER PUBLICATIONS

Notice of Reasons for rejection for Japanese Patent Application No. 2017-559032, mailed Jan. 14, 2020.

Decision on Rejection for Chinese Patent Application No. 201680027690.7, mailed Jun. 2, 2020.

Second Office Action for Chinese Patent Application No. 201680027690.7, mailed Sep. 18, 2019.

Notice of Reasons for Rejection for Japanese Patent Application No. 2017-559032, mailed on Nov. 9, 2020, original and translated, 8 pages.

Chinese Search Report; State Intellectual Property Office; Peoples Republic of China; Chinese Patent Application No. 201680027690.7, Dec. 27, 2018; 7 pages.

Chinese Office Action (1st); State Intellectual Property Office; Peoples Republic of China; Chinese Patent Application No. 201680027690.7, Dec. 27, 2018; 19 pages.

International Search Report; European Patent Office; International Application No. PCT/US16/32349; Jul. 29, 2016; 5 pages.

Written Opinion of the International Searching Authority; International Application No. PCT/US16/32349; Jul. 29, 2016; 5 pages.

* cited by examiner

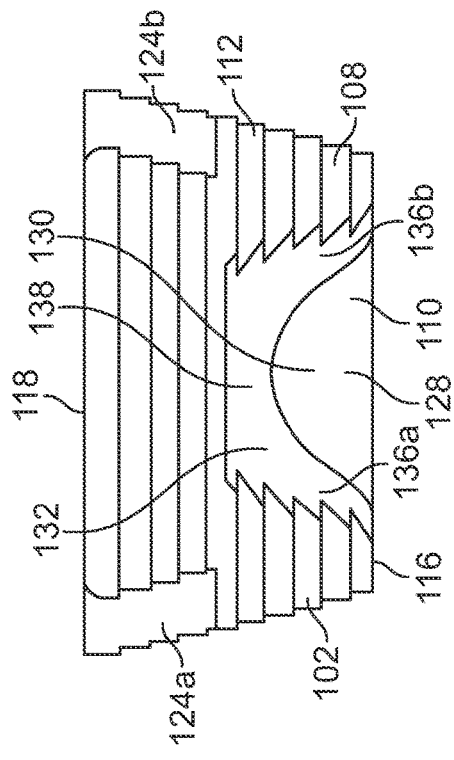
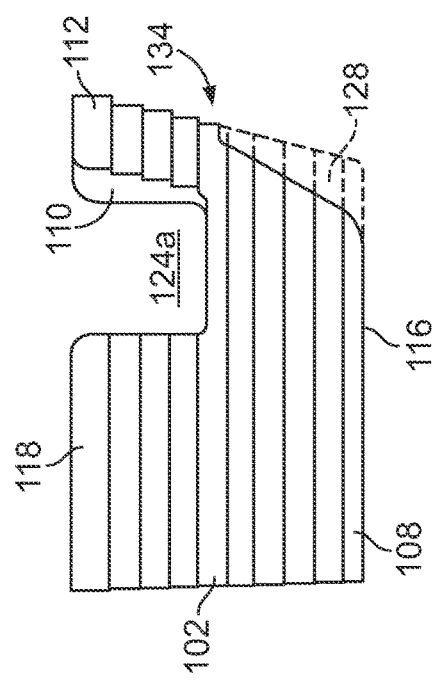
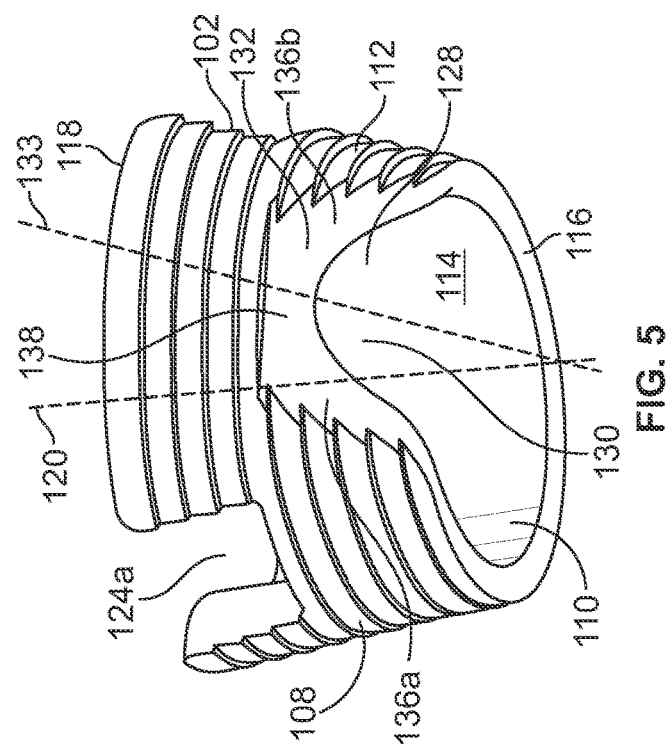

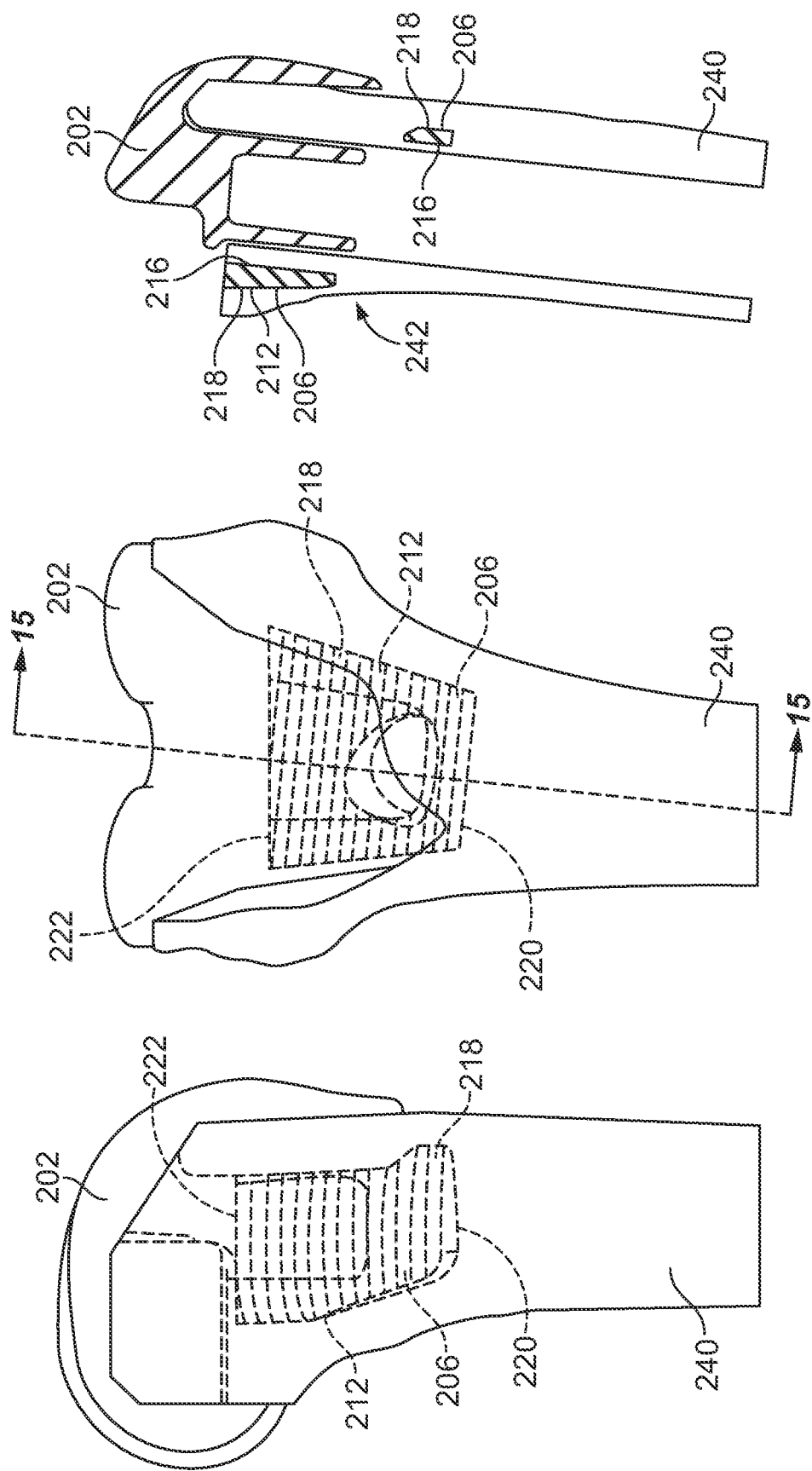

ANATOMICALLY RELIEVED AUGMENTS

CROSS-REFERENCE TO RELATED APPLICATION

The present application is a continuation of pending U.S. patent application Ser. No. 16/216,437, filed Dec. 11, 2018, which is a continuation of U.S. patent application Ser. No. 15/572,943 filed Nov. 9, 2017, now abandoned, which is a U.S. National Phase of International PCT Application No. PCT/US2016/032349 filed May 13, 2016, which claims the benefit of U.S. Provisional Application Ser. No. 62/160,891 filed May 13, 2015, the contents of each application are incorporated herein by reference in their entirety.

BACKGROUND

Embodiments of the present application generally relate to orthopedic augments. More particularly, but not exclusively, embodiments of the present application relate to anatomically shaped orthopedic augments that are configured to address unequal loading conditions and provide enhanced flexibility in placement within the associated bone canal.

Metaphyseal and/or diaphyseal augments typically assist in preventing loosening and/or subsidence of an articular implant/component, such as, for example, an implanted tibia baseplate. Such augments can help distribute loads exerted on or by the articular implant through the bone, with the articular component maintaining fixation, which can result in a longer implant life.

One of the primary forces attributed to early failures of orthopedic implants, particularly in the tibia, is torsional stress. Moreover, torsional stresses can shear the articular implant-bone interface (cemented or un-cemented) apart, which can facilitate premature or early failure of the implant. Other forces, such as shear forces, can also contribute to similar premature or early failure of the articular implant-bone interface. Additionally, compressive loads, particularly unequal loads to a median plane (i.e. medial loading) of the articular implant-bone interface, can also cause subsidence and early failures of the articular implant.

Additionally, too much cortical contact with the augment can, as a consequence of carrying too much of the load, stress shield the articular components of the bone interface. Such situations can result in bone resorption, which can contribute to early failure of the implant. Additionally, unequal cortical contact due to lack of conformity or fit can load a particular region of the bone, and thereby relieve the articular implant-bone interface in a similar region. In at least certain situations, such unequal loads or contact can act as a fulcrum, which can facilitate bone-interface failures for both the augment and the articular implant.

BRIEF SUMMARY

An aspect of the present application is an augment for implantation in association with an orthopedic implant device in a bone, the augment having an augment wall that includes an outer portion, an inner portion, a distal end, and a proximal end. The inner portion of the augment wall defines an inner region of the augment that is sized to receive placement of one or more components of the orthopedic implant device. The distal end at the outer portion has a first shape that is configured to generally conform to the shape of a-metaphyseal-diaphyseal junction of a canal of the bone. Additionally, the proximal end at the outer portion has a second shape that is configured to generally conform to a shape of the metaphyseal region of the canal of the bone. Further, the first shape has a different shape and size than the second shape. The augment further includes at least one relief that extends from at least one of the proximal end or the distal end of the augment wall. Additionally, at least one relief is adapted to prevent, when the augment is implanted in the bone, contact between a portion of the augment wall and an adjacent wall of the bone.

BRIEF DESCRIPTION OF THE FIGURES

The description herein makes reference to the accompanying figures wherein like reference numerals refer to like parts throughout the several views.

FIG. 3 illustrates an isometric view of an anatomically relieved tibial augment according to an embodiment of the present application.

FIG. 4 illustrates a medial-lateral view of the anatomically relieved tibial augment shown in FIG. 3.

FIG. 5 illustrates a posterior-anterior view of the anatomically relieved tibial augment shown in FIG. 3.

FIG. 13 illustrates a medial-lateral view of a portion of an exemplary femoral implant device having an anatomically relieved femoral augment positioned on a prepared femoral bone.

FIG. 14 illustrates an anterior-posterior view of the portion of the femoral implant device and the anatomically relieved femoral augment shown in FIG. 13 positioned on the prepared femoral bone.

FIG. 15 illustrates a medial-lateral cross sectional view, taken along line A-A of FIG. 14, of the portion of the femoral implant and anatomically relieved femoral augment on the prepared femoral bone.

Figure 2:
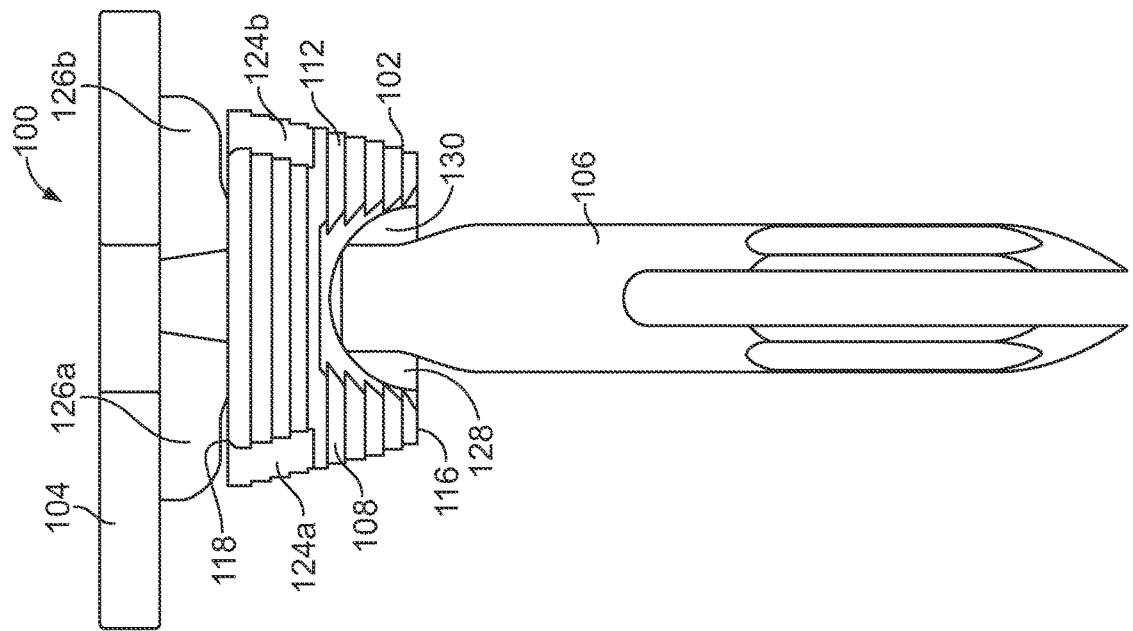
FIG. 2 illustrates a posterior-anterior view of the tibial implant device and anatomically relieved tibial augment shown in FIG. 1.

The foregoing summary, as well as the following detailed description of certain embodiments of the present application, will be better understood when read in conjunction with the appended drawings in which like reference numbers indicate like features, components and method steps. For the purpose of illustrating the invention, there is shown in the drawings, certain embodiments. It should be understood, however, that the present invention is not limited to the arrangements and instrumentalities shown in the attached drawings.

DETAILED DESCRIPTION

Certain terminology is used in the foregoing description for convenience and is not intended to be limiting. Words such as "upper," "lower," "top," "bottom," "first," and "second" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

Figure 1:
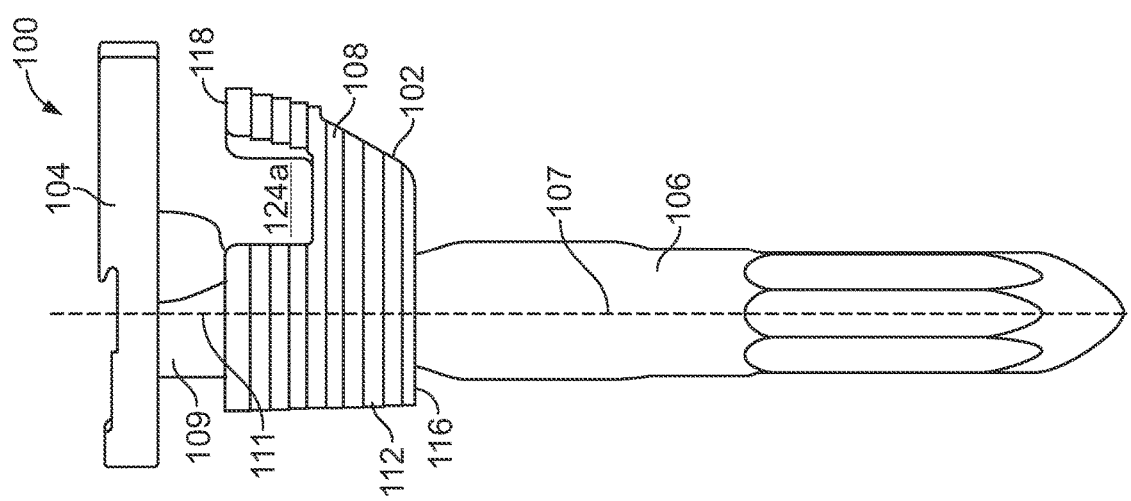
FIG. 1 illustrates a medial-lateral view of a tibial articular implant having an anatomically relieved tibial augment according to an embodiment of the present application.
Figure 7:
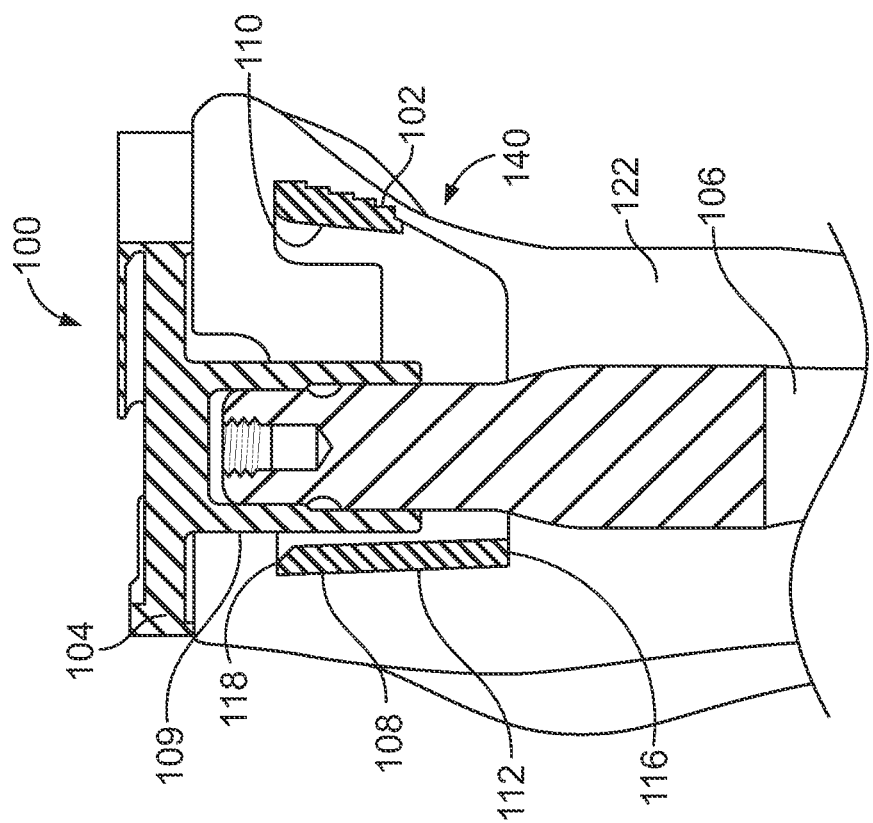
FIG. 7 illustrates a cross sectional view, taken along line A-A of FIG. 6, of the bone and tibial implant device, including the anatomically relieved tibial augment.

FIGS. 1 and 2 illustrate medial-lateral and posterior-anterior views, respectively, of a tibial implant device 100 having an anatomically relieved tibial augment 102 according to an embodiment of the present application. In the depicted embodiment, the tibial implant device 100 is a tibial articular assembly that includes a tibial (articular) baseplate 104, the tibial augment 102, and a stem 106. The stem 106, which can extend along a central stem axis 107, can be directly or indirectly coupled to the tibial baseplate 104, such as, for example, coupled to a tray stein 109 (FIG. 7). According to certain embodiments, the tibial implant device 100 can also include an offset/angled coupler, which can offset at least the central stem axis 107 relative to a central tray stem axis 111 of the tray stem 109 of the base plate 104. The tibial implant device 100 can also include other components, such as, for example, intramedullary stems and other augments that can be assembled to the tibial implant device 100.

The depicted tibial implant device 100 is structured to be cemented into and through the tibial augment 102 and onto a prepared proximal tibia of a patient. Further, while FIGS. 1 and 2 illustrate the tibial augment 102 positioned on or about a tibial implant device 100 in a non-implanted state or condition, the tibial augment 102 can be implanted in a bone of the patient prior to implantation of the remainder of the tibial implant device 100.

FIGS. 3-5 illustrate isometric, medial-lateral, and posterior-anterior views, respectively, an exemplary tibial augment 102 according to certain embodiments of the present application. A variety of different augments can be used for the tibial augment 102, including, for example, a cone or sleeve augment, among other augments. Further, the tibial augment 102 can have a variety of shapes and sizes. The tibial augment 102 includes an augment wall 108 that has an inner portion 110 and an outer portion 112. The inner portion 110 of the augment wall 108 can generally define an inner region 114 of the tibial augment 102, which can extend between at least a portion of the distal and proximal ends 116, 118 of the tibial augment 102. As indicated by at least FIGS. 1, 2, and 7, the inner portion 110 of the augment wall 108 can be sized to receive passage and/or placement of at least a portion of the stem 106, a tray stem 109 of the baseplate 104, an offset/angled coupler, and/or other components of the tibial implant device 100 during implantation of the tibial implant device 100 in a patient.

The outer portion 112 of the tibial augment 102 can have a variety of shapes and sizes. For example, according to certain embodiments, an augment wall 108 of the tibial augment 102 can have a generally cylindrical or conical shape as the augment wall 108 extends between a distal end 116 and a proximal end 118 of the tibial augment 102. However, according to other embodiments, the augment wall 108 can be constructed to generally conform to the shapes of different portions of the bone, such as, for example, the conical shape of the tibia bone, and/or to the shape of the inner wall of the intramedullary canal or prepared opening in the bone in which the tibial augment 102 will be implanted. Thus, variations among and/or along at least the augment wall 108 of the tibial augment 102 that accommodate such shapes of the bone, intramedullary canal, and/or the prepared opening can enhance the flexibility in the placement of the tibial augment 102 in the bone, and reduce or minimize the tibial augment 102 from hindering the ability to position an associated articular component relative to a joint line, while also not hindering joint balance (flexion-extension balance) and rotation of each component relative to the patella-femoral joint. Additionally, according to certain embodiments, the tibial augment 102 can be symmetrical about at least one midline that is generally perpendicular to a central augment axis 120 of the tibial augment 102.

To generally accommodate the cortical shape(s) of the tibia bone, the intramedullary canal of the tibia, and/or the shape of the prepared opening in the tibia bone in which the tibia augment 102 is to be implanted, the shape of various portions or sides of the augment wall 108 at the distal and/or proximal ends 116, 118, as well as the shapes of the sides of the augment wall 108 therebetween, can be different and/or vary. According to such embodiments, such variances or inconsistencies among and/or along the sides or areas of the tibial augment 102 can preclude the augment wall 108 of the tibial augment 102 from having a generally uniform cylindrical or conical shape. Further, according to certain embodiments, the outer portion 112 of the augment wall 108 of the tibial augment 102 can be configured such that at least the distal end 116, or diaphyseal end, of the tibial augment 102 generally conforms to the general shape of the metaphyseal-diaphyseal junction of the tibia bone 122, and at least the proximal end 118 of the tibial augment 102 generally conforms to the general shape or profile of the metaphyseal region of the tibia bone 122. According to other embodiments, the distal end 116 and/or proximal end 118 can be shaped to provide other cross-sectional shapes that facilitate the ability of the tibial augment 102 to conform to the size and/or shape of at least a portion of the intramedullary canal 124 of the tibia bone 122 and/or of the prepared opening in the tibia bone 122. Such conforming of the tibial augment 102 may not be limited to the physical shape(s) of each section of the outer portion 112 of the tibial augment 102 mating or matching the shape of the adjacent portion of the wall of the intramedullary canal 124, but instead can include being shaped to operably align a central augment axis 120 of the tibial augment 102 with, or at a selected position away from, a reference axis, including, for example, a longitudinal axis of the intramedullary canal 124, and/or the central stem axis 107, among other reference axes. Additionally, the portion of the tibial augment 102 that is shaped to generally conform to the shape or profile of the metaphyseal region can be located at distance away, in the metaphyseal direction, from the portion of the tibial augment 102 that conforms to the general shape or profile of the metaphyseal-diaphyseal junction that is about the same as the distance between the metaphyseal region and metaphyseal-diaphyseal junction of the tibia bone 122.

As shown in at least FIGS. 1-5, according to certain embodiments, the augment wall 108 can further include at least one opening 124a, 124b that is configured to accommodate placement of a component of the tibial augment 102. For example, according to the illustrated embodiment, the tibial augment 102 can include two openings 124a, 124b that are sized to accommodate at least the passage and/or placement of at least a portion of the keel(s) 126a, 126b of the tibial baseplate 104.

The outer portion 112 of the augment wall 108 can also include one or more reliefs 128 that are positioned at least around the distal end 116 and/or the proximal end 118 of the tibial augment 102. According to the illustrated embodiment, the relief 128 can remove at least a portion of the augment wall 108 so as to reduce or otherwise alter the shape of at least a profile of the tibial augment 102. For example, dashed lines in FIG. 3 illustrate a portion of the tibial augment 102 that can be removed by the recess 128, and the resulting profile provided by inclusion of the relief 128. As discussed below, removing, altering, and/or contouring the shape and/or size of the tibial augment 102 via inclusion of one or more reliefs 128 that can increase the degree of freedom that can be attained in the placement and/or sizing of the tibial augment 102 in the tibia bone 122, intramedullary canal, and/or a shaped or prepared opening in the tibia bone 122.

According to certain embodiments, the recess 128 can be configured to extend through the augment wall 108 so as to include an aperture 130 that exposes at least a portion of the inner region 114. Further, the relief 128 can also include one or more relief walls 132, such as, for example, opposing sidewalls 136a, 136b and an upper wall 138 that extends around the aperture 130. The relief walls 132 can reduce the thickness of the augment wall 108 at or around the aperture 130. Moreover, the augment wall 108 can have a material thickness between the relief wall 132 and the opposing inner portion 110 of the augment wall 108 that is less than the thickness between opposing outer and inner portions 110, 112 of the augment wall 108.

The sidewalls 136a, 136b and upper wall 138 of the relief wall 132 can have a variety of different shapes and orientations that can, in at least certain situations, increase the degree of freedom in the positioning and/or sizing of the tibial augment 102 in the bone 122 that can be attained via use of the relief 128. For example, in the illustrated embodiment, the upper wall 138 has a generally curved or arced shape, while the sidewalls 136a, 136b generally extend toward each other from opposite directions before reaching the upper wall 138. Additionally, as shown in FIG. 3, according to the illustrated embodiment, the relief 128 can be configured such that a portion of the relief wall 132 has an angled or tapered profile that extends inwardly toward the distal end 116, and which provides a larger or stepper incline than can have otherwise been provided by the augment wall 108 without the inclusion of the relief 128 (as indicated by a comparison of the adjacent solid and dashed lines in FIG. 3).

FIGS. 4 and 5 illustrate a relief 128 having an aperture 130 that extends through a portion of the distal end 116 of the tibial augment 102, and a relief wall 132 that extends along a portion of the tibial augment 102 and about the aperture 130. However, although the relief 128 of the depicted embodiment includes an aperture 130 in the augment wall 108, according to certain embodiments, the relief 128 can extend into the augment wall 108 to a degree that prevents the formation of such an aperture 130 in the relief 128. Further, the aperture 130 of the relief 128 and at least a portion of the relief wall 132 can extend along a central relief axis 133 that is generally parallel to the adjacent portion of the augment wall 108 in which the aperture 130 is positioned. Further, the central relief axis 133 can be non-perpendicular to the central augment axis 120 and/or the central stem axis 133 that can extend into/through the inner region 114 of the tibial augment 102.

The degree to which the relief 128 extends along the augment wall 108 can vary. For example, in the illustrated embodiment, the relief 128 extends from the distal end 116 of the augment wall 108 to generally a mid-region 134 of the augment wall 108, the mid region 134 being located a midpoint or area between the distal and proximal ends 116, 118 of the tibial augment 102. Again, while the relief 128 depicted in FIGS. 4 and 5 extends from the distal end 116 of the tibial augment 102, according to other embodiments, a relief, in addition to or in lieu of the relief 128 depicted in FIGS. 4 and 5, can extend from the proximal end 118 of the tibial augment 102.

Figure 6:
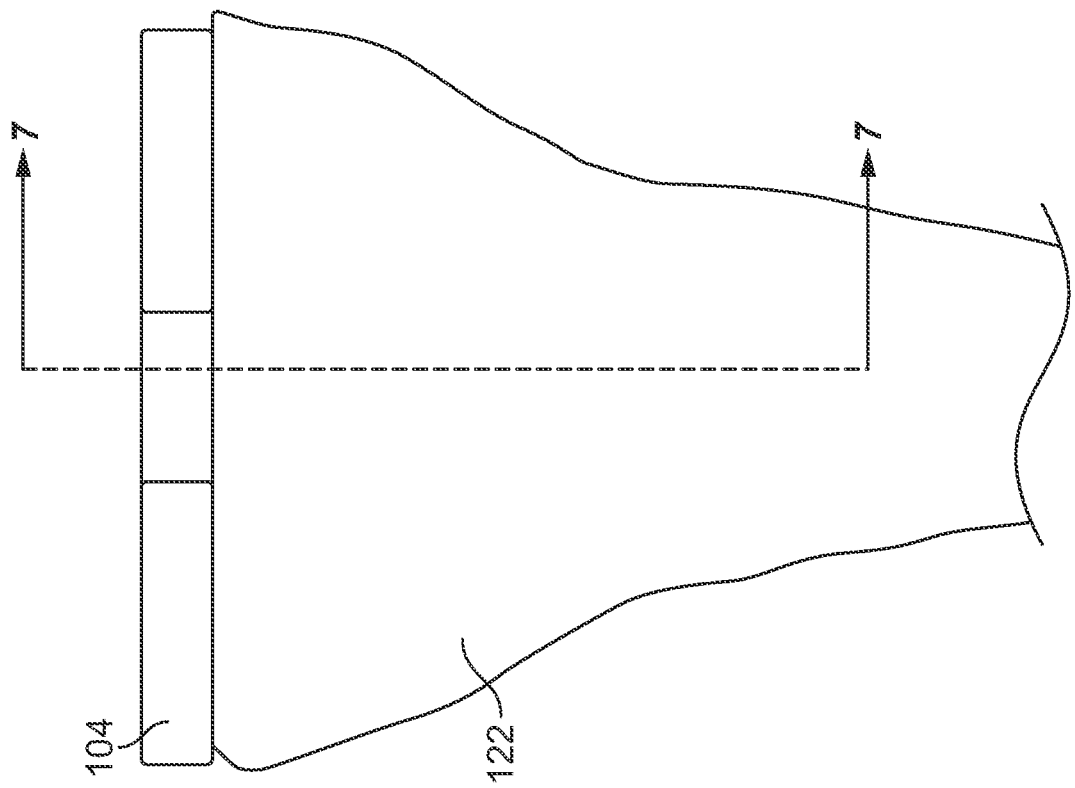
FIG. 6 illustrates a posterior-anterior view of a tibial implant device on a prepared implant bone.

FIG. 7 provides an example of a relief 128 of a tibial augment 102 being configured to accommodate the cortical shape and/or configuration of the tibia bone 122 and/or intramedullary canal, as depicted in FIG. 6. As illustrated, the reduction in the size of the profile of at least a portion of the tibial augment 102, and, moreover, the resulting adjustment in the shape of the tibial augment 102, as provided by the relief 128, can be configured to at least assist in the tibial augment 102 being anatomically shaped and/or to assist in contouring or otherwise shaping the tibial augment 102 avoid cortical bone contact, such as, for example, avoiding contact with the cortical bone in the metaphyseal-diaphyseal junction 140. Further, the relief 128 can be sized or otherwise configured to prevent the tibial augment 102 from engaging the asymmetric morphology of the tibia bone 122. Additionally, as also shown by FIG. 7, the inclusion of the relief 128 can at least assist in the tibial augment 102 from avoiding contact with the implant construct, including, for example, contact with the tibial implant device 100 that can be associated with misalignment of the intramedullary canal with the metaphyseal and/or the diaphyseal region(s) of the tibia bone 122.

Figure 8:
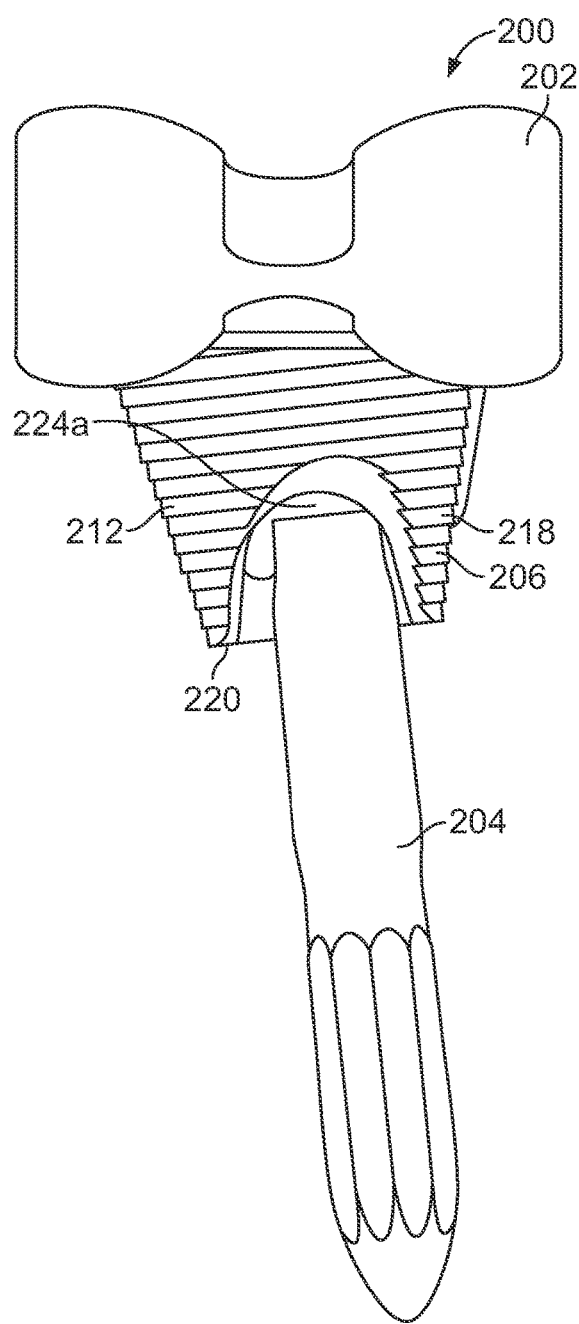
FIG. 8 illustrates a posterior-anterior view of a femoral implant, device having an anatomically relieved femoral augment according to an embodiment of the present application.
Figure 9:
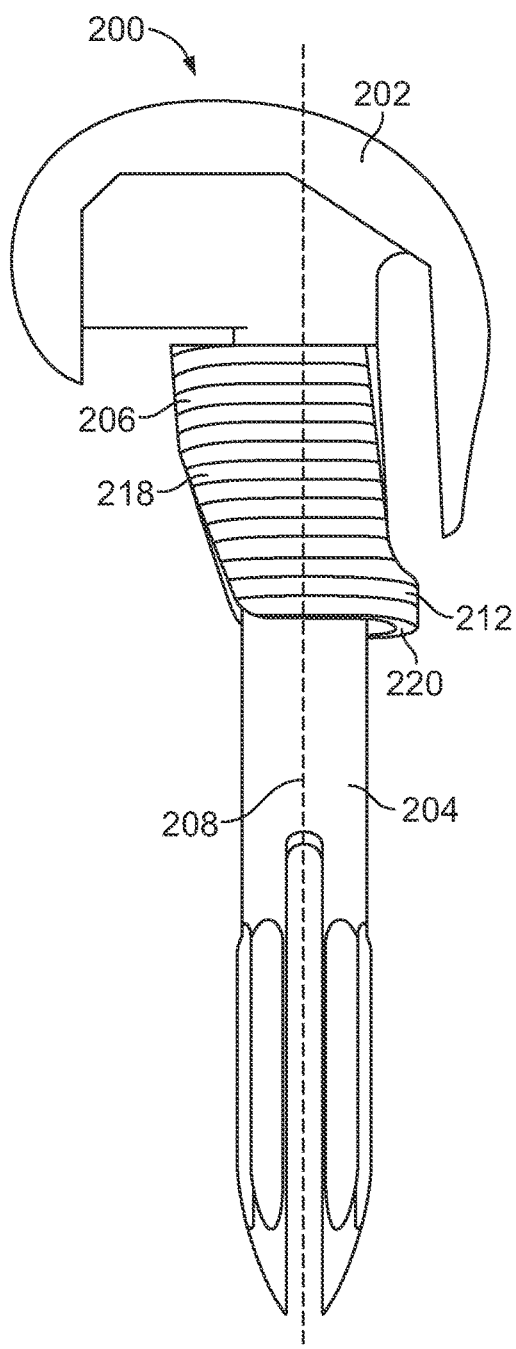
FIG. 9 illustrates a medial-lateral view of the femoral implant device and anatomically relieved femoral augment shown in FIG. 8.

FIGS. 8 and 9 illustrate posterior-anterior and medial-lateral views, respectively, of a femoral implant device 200. The illustrated femoral implant device 200 includes a femoral articular component 202, an intramedullary stem 206, and a femoral augment 206 according to an illustrated embodiment of the present application. The femoral implant device 200 can include other components, including, but not limited to, a distal augment and/or a posterior augment. The intramedullary stem 206, which can extend along a central stem axis 208, can be directly or indirectly coupled to the femoral articular component 202, such as, for example, coupled to a component stem of the femoral articular component 202. According to certain embodiments, the femoral implant device 200 can include an offset/angled coupler, which can offset at least the central stem axis 208 relative to an axis the component stem.

The depicted femoral implant device 200 is structured to be cemented into and through the femoral augment 206 and onto a prepared distal femur of a patient. Further, while FIGS. 8 and 9 illustrate the femoral augment 206 positioned on or about a femoral implant device 200 in a non-implanted state or condition, the femoral augment 206 can be implanted in a bone of the patient prior to implantation of the remainder of the femoral implant device 200. Thus, an inner region 219 of the femoral augment 206 can be sized to receive passage and/or placement of at least a portion of the intramedullary stem 206 and/or other components of the femoral implant device 200, including, for example, an offset/angled coupler and/or a component stem of the femoral articular component 202, during implantation of the femoral implant device 200 in a patient.

Figure 10:
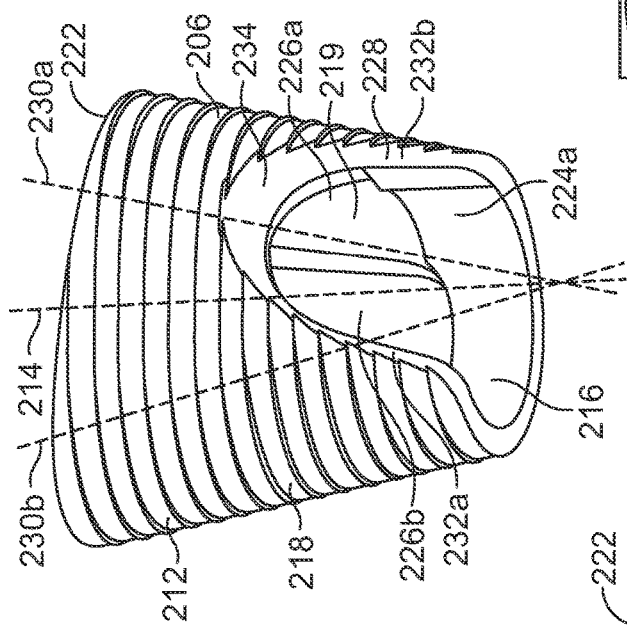
FIG. 10 illustrates an isometric view of an anatomically relieved femoral augment according to an embodiment of the present application.
Figure 12:
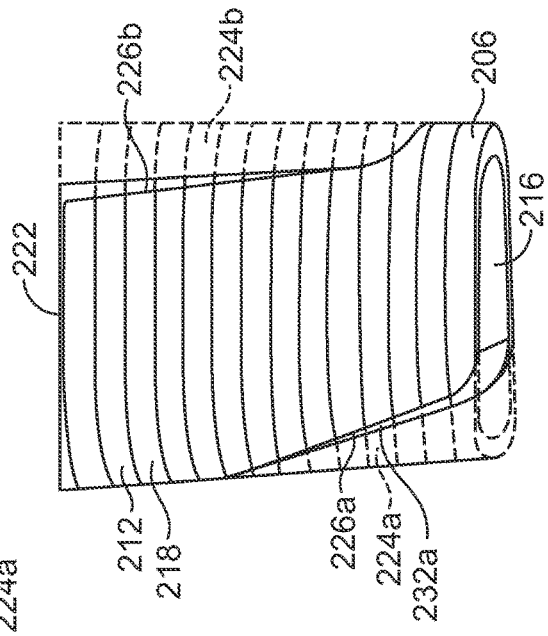
FIG. 12 illustrates a posterior-anterior view of the anatomically relieved femoral augment shown in FIG. 10.
Figure 11:
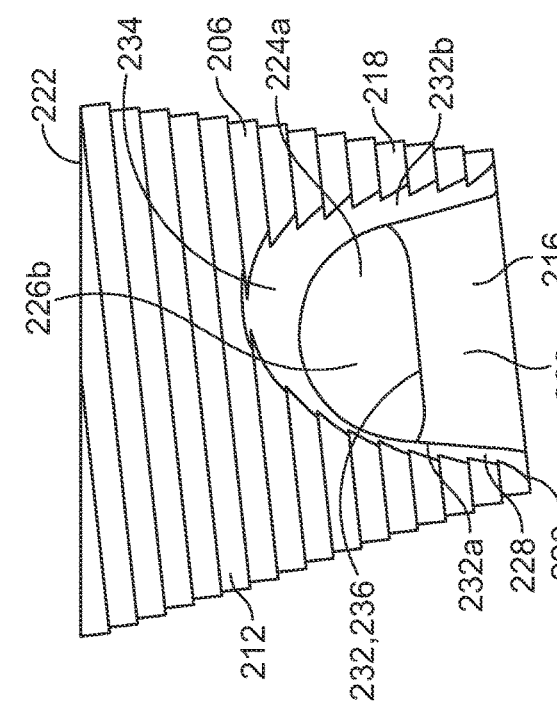
FIG. 11 illustrates a medial-lateral view of the anatomically relieved femoral augment shown in FIG. 10.

FIGS. 10-12 illustrate an example of a femoral augment 206 according to an illustrated embodiment of the present application. A variety of different augments can be used for the femoral augment 206, including, for example, a cone or sleeve augment, among other augments. Further, the femoral augment 206 can have a variety of shapes and sizes. The femoral augment 206 can include an augment wall 212 that extends about a central augment axis 214 of the femoral augment 206. The augment wall 212 has an inner portion 216 and an outer portion 218. The inner portion 216 of the augment wall 212 can generally define an inner region 219 of the femoral augment 206. At least a portion of the inner region 219 can extend between a distal end 220 and a proximal end 222 of the femoral augment 206. The inner region 219 can be sized to receive placement of at least one or more components of the femoral augment 206, such as, for example, the intramedullary stein 206, an offset/angled coupler, and/or the component stem of the femoral articular component 202, and junctions there between, among other components.

The outer portion 218 of the augment wall 212 can be shaped to generally fit the cortical shape of a distal femur and/or a portion of the intramedullary canal of the femur. Thus, according to certain embodiments, a diaphyseal or distal end 220, of the femoral augment 206 can be shaped to generally conform to the general shape of the metaphyseal-diaphyseal junction of femoral bone. Further, the opposing proximal end 222 of the femoral augment 206 can be configured to generally conform to the general shape or profile of the metaphyseal region of the femoral bone. According to other embodiments, the distal end 220 and/or proximal end 222 can be shaped to provide other cross-sectional shapes that facilitate the ability of the femoral augment 206 to conform to the size and/or shape of at least a portion of the femur and/or the intramedullary canal of the femur. Such conforming may not be limited to the physical shape(s) of each section of the outer portion 218 of the augment mating or matching the shape of the adjacent portion of the inner wall of the intramedullary canal of the femoral bone, but instead can include being shaped to generally align with a central augment axis 214 of the femoral augment 206, or at a selected position away from a reference axis, including, for example, a longitudinal axis of the intramedullary canal of the femur and/or the central stem axis 208, among other reference axes. Additionally, the portion, of the femoral augment 206 that is shaped to generally conform to the shape or profile of the metaphyseal region of the femur and/or the intramedullary canal of the femur can be located at distance away, in the metaphyseal direction, from the portion of the femoral augment 206 that conforms to the general shape or profile of the metaphyseal-diaphyseal junction that is about the same as the distance between the metaphyseal region and metaphyseal-diaphyseal junction of the femur.

To generally accommodate the cortical shape(s) of femur and/or the medullary canal of the femur, including, for example, the shape at both the metaphyseal-diaphyseal junction and at metaphyseal region of the femur, as well as shapes therebetween, different areas or sides of the outer portion 218 of the augment wall 212 can have different shapes. Additionally, the shapes along such different areas or sides of the outer portion 218 of the augment wall 212 can also vary between the distal and proximal ends 220, 222 of the femoral augment 206. Such variances or inconsistencies among and/or along the sides or areas of the femoral augment 206 can preclude the augment wall 212 of the femoral augment 206 from having a generally uniform cylindrical or conical shape. However, according to other embodiments, the femoral augment 206 can have a generally cylindrical or conical shape.

As shown by at least FIGS. 10-12, the outer portion 218 of the augment wall 212 can include one or more reliefs 224a, 224b that are positioned at least around a portion of the distal end 220 and/or the proximal end 222 of the femoral augment 206. According to the illustrated embodiment, the reliefs 224a, 224b can provide a recess and/or aperture 226a, 226b in the augment wall 212, and a relief wall 228 that reduces the thickness of the augment wall 212 at or around the apertures 226a, 226b. As shown in FIGS. 10-12, in the depicted embodiment, the femoral augment 206 includes a first relief 224a that extends from the distal end 220 and toward the proximal end 222 of the femoral augment 206, and another, second relief 224b on a generally opposing side of the augment wall 212 that extends in an opposite direction, and more specifically, extends from the proximal end 222 toward the distal end 220 of the femoral augment 206. As illustrated, in the depicted example, each relief 224a, 224b extends to an area adjacent, or in relatively close proximity to, the opposing distal or proximal end 220, 222 of the augment 206.

The relief wall 228 for each relief 224a, 224b can extend along the femoral augment 206 and at least about the aperture 226a, 226b. Further, the augment wall 212 can have a material thickness between the relief walls 228 and the inner portion 216 of the augment wall 212 that is less than the thickness between opposing inner and outer portions 216, 218 of the augment wall 212. Further, although the reliefs 224a, 224b of the depicted embodiment each include an aperture 226a, 226b in the augment wall 212, according to certain embodiments, one or both of the reliefs 224a, 224b can extend into the augment wall 212 to a degree that prevents the formation of such an aperture 226a, 226b.

According to the illustrated embodiment, the apertures 226a, 226b and/or at least a portion of the relief walls 228 can extend along an associated central relief axis 230a, 230b that is generally parallel to the adjacent portion of the augment wall 212 in which the apertures 226a, 226b and/or relief walls 228 is/are positioned. Further, the central relief axes 230a, 230b can be non-perpendicular to the central augment axis 214 of the femoral augment 206 and/or to the central stem axis 208 of the intramedullary stem 204 that can extend into/through the inner region 219 of the femoral augment 206.

As shown in FIGS. 10-12, according to the illustrated embodiment, the relief walls 228 of the reliefs 224a, 224b can each include opposing sidewalls 232a, 232b and an adjoining upper wall 234. The sidewalls 232a, 232b and upper wall 234 can have a variety of different shapes and orientations that can, in at least certain situations, facilitate the freedom of positioning and/or sizing that is attained via use of the reliefs 224a, 224b. For example, as shown by at least FIG. 11, in the illustrated embodiment, the upper wall 234 for the first relief 224a can have a generally curved or arced shape, while the upper wall 234 of the second relief 224b includes a generally flat section 236. Further, as shown in at least FIG. 12, at least a portion of the sidewalls 232a, 232b of the reliefs 224a, 224b can have angled or tapered profiles that extend inwardly toward the associated distal end 220 or proximal end 222, which can assist in providing the femoral augment 206 with a narrower or thinner profile in those regions than would be provided in the absence of the reliefs 224a, 224b (as indicated by the dashed lines in FIG. 12).

The anatomical shape of the tibial or femoral augments 102, 206, as well as the inclusion of the reliefs 128, 224a, 224b, can increase the available choices or freedom in the positioning and/or sizing of the augments 102, 206 in the corresponding prepared tibial or femur bone, or shaped opening in the tibial or femur bone and/or the associated intramedullary canal in which the tibial or femoral augment 102, 206 is implanted. As discussed, the inclusion of the reliefs 128, 224a, 224b can reduce the profile and/or size of the tibial femoral augment 102, 206 at least at the distal end 116, 220 and proximal end 118, 222, and/or along the opposing sides of the tibial or femoral augment 102, 206. Further, the reliefs 128, 224a, 224b can be configured such that the augments 102, 206 are configured to accommodate certain characteristics in the shape of the bone or bone canal in which the augments 102, 206 can be placed. For example, the inclusion of the reliefs 128, 224a, 224b can at least assist in the augments 102, 206 avoiding contact with certain portions of the bone, such as, for example, preventing the femoral augment 206 from engaging the asymmetric morphology of the femur.

When an anatomically shaped tibial or femoral augment 102, 206 that includes a relief(s) 128, 224a, 224b, as discussed herein, is subjected to placement at relatively shallow depths in the shaped or prepared tibial or femur, such as when an implant device 100, 200 is near the epiphysis of the bone, cancellous bone can be the primary, and possibly only, contact to the load bearing surfaces of the tibial or femoral augment 102, 206. Further, as the depth of the prepared opening in the tibial or femoral bone increases conformity, proximity of the prepared opening and placement of the anatomically shaped augments 102, 206 having the reliefs 128, 224a, 224b to the cortical bone can also increase. Such conformity and consistency of cancellous and/or cortical bone contact throughout a depth variation of deployment of the tibial or femoral augments 102, 206 can at least assist in enhancing the evenness in load distribution, as well as enhance resistance implant failure, that can otherwise be attributed to loosening and/or subsiding due to one or more of the forces, such as, for example, compressive, shear, and/or torsion forces, that can be associated with implant devices and associated components. Accordingly, the anatomically shaped tibial and femoral augment augments 102, 206 can be configured, including shaped and/or via the inclusion of reliefs 128, 224a, 224b, to prevent or minimize the occurrence of point contact between the augments 102, 206 and the adjacent cortical wall of the bone. The prevention of such point contact can include preventing misaligned or unequal circumferential load sharing about the cortical wall. Further, by preventing point contact, the augments 102, 206 can prevent or otherwise minimize the potential for the augment 102, 206 to penetrate through, or otherwise violate, the adjacent conical wall of the bone.

Shaping the tibial and femoral augments 102, 206 to generally conform to, or accommodate, changes and/or variances in the shape of the tibia and femoral bone, respectively, and/or the intramedullary canal 124 of those bones, can prevent or minimize the extent to which the tibial or femoral augments 102, 206 are subjected to unequal loading conditions. Further, by shaping different portions or areas of the tibial and femoral augments 102, 206 to generally conform to or otherwise accommodate the shape of at least an adjacent inner wall of the associated bone canal or cavity, the generally anatomically shaped augments 102, 206 discussed herein can reduce the impact forces on the corresponding articular implant-bone interface by distributing such forces or loads over a relatively larger surface area. More specifically, for example, such conforming configurations of the augments 102, 206 can improve resistance to torsional stress by equally distributing such forces circumferentially.

FIGS. 13 and 14 illustrate medial-lateral and anterior-posterior views, respectively, of a femoral articular component 202 of an exemplary femoral implant device 202 having an anatomically relieved femoral augment 206, and which is positioned on a prepared femoral bone 240. Further, FIG. 15 illustrates a medial-lateral cross sectional view of the portion of the femoral articular component 202 and the anatomically relieved femoral augment 206 on the prepared femoral bone 240, as taken along line A-A of FIG. 14. As shown in FIG. 13, a first relief 224a can be configured to generally conform the shape or profile of the femoral augment 206 to the shape of the femoral bone 240 at the metaphyseal-diaphyseal junction 242, and moreover, to avoid contact with the cortical bone in the metaphyseal-diaphyseal junction 242. Further, as shown, the inclusion of the reliefs 224a, 224b can at least assist in the femoral augment 206 avoiding contact with the implant construct, including, for example, contact with the femoral articular component 202 that can be associated with intramedullary canal misalignment with the metaphyseal and/or the diaphyseal region(s) of the femoral bone 240. For example; as shown, the second relief 224b of the femoral augment 206 can be shaped to prevent or otherwise minimize the femoral augment 206 from contacting an inner portion 216 of the femoral implant device 200, such as, for example, an inner portion of the articular implant construct, while still providing a segment of the femoral augment 206 at the distal end 220 of the femoral bone 240 that can be implanted at a positioned in a prepared portion or cavity of the bone 240. Thus, the reliefs 224a, 224b, as illustrated, can be constructed to allow for a degree of rotational freedom in the angular position of the implanted femoral augment 206 about at least the central augment axis 214 while still allowing the femoral augment 206 to generally conform to the shape of the femoral bone 240 and still prevent, if desired, contact between the femoral augment 206 and the inner portion 216 of the femoral implant device 200.

While the invention has been described in connection with what is presently considered to be the most practical and preferred embodiment, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

The invention claimed is:

1. A tibial implant comprising:
a tibial baseplate including a top surface and a bottom surface;
a stem extending from the bottom surface; and
an augment arranged and configured to receive the stem therethrough, the augment including:
an augment wall having an outer portion, an inner portion, an anterior side, a posterior side, a distal most end, and a proximal most end opposite the distal most end, the inner portion defining an inner region of the augment, the inner region sized to receive the stem so that the proximal most end of the augment wall is positioned adjacent to the bottom surface of the tibial baseplate in use, the inner region extending along a longitudinal axis; and
a relief formed in the augment wall and extending through the augment wall from the outer portion to the inner portion, the relief extending from the distal most end toward the proximal most end and along a relief axis.

2. The tibial implant of claim 1, wherein the relief axis is oblique to the longitudinal axis and extends away from the longitudinal axis in a distal-to-proximal direction.

3. The tibial implant of claim 1, wherein the outer portion is stepped.

4. The tibial implant of claim 1, wherein the relief further includes a relief wall, the relief wall being inwardly tapered to reduce a profile size of the augment.

5. The tibial implant of claim 1, wherein the relief has a distal end portion and a proximal end portion, and wherein the distal end portion is wider than the proximal end portion.

6. The tibial implant of claim 1, wherein the relief is formed in the posterior side of the augment wall.

7. The tibial implant of claim 1, wherein the relief terminates midway between the distal most end and the proximal most end.

8. The tibial implant of claim 1, further comprising a pair of openings extending distally from the proximal most end, wherein the pair of openings is configured to receive placement of a pair of keels extending from the tibial baseplate.

9. The tibial implant of claim 1, wherein the anterior side extends at a first angle relative to the longitudinal axis, wherein the posterior side extends at a second angle relative to the longitudinal axis, and wherein the first angle is different from the second angle.

10. The tibial implant of claim 1, further comprising a second relief formed in the augment wall and extending through the augment wall from the outer portion to the inner portion, the second relief extending from the proximal most end toward the distal most end and along a second relief axis, wherein the second relief axis is oblique to the longitudinal axis and extends away from the longitudinal axis in a proximal-to-distal direction.

11. The tibial implant of claim 1, wherein the second relief terminates midway between the proximal most end and the distal most end.

12. A femoral implant comprising:
a femoral articular component including an articular surface and a proximal surface opposite the articular surface;
a stem extending from the proximal surface; and
an augment arranged and configured to receive the stem therethrough, the augment including:
an augment wall having an outer portion, an inner portion, an anterior side, a posterior side, a distal most end, and a proximal most end opposite the distal most end, the inner portion defining an inner region of the augment, the inner region sized to receive the stem so that the distal most end of the augment wall is positioned adjacent to the proximal surface of the femoral component in use, the inner region extending along a longitudinal axis; and
a relief formed in the augment wall and extending through the augment wall from the outer portion to the inner portion, the relief extending from the proximal most end toward the distal most end and along a relief axis.

13. The femoral implant of claim 12, wherein the relief axis is oblique to the longitudinal axis and extends away from the longitudinal axis in a proximal-to-distal direction.

14. The femoral implant of claim 12, wherein the outer portion is stepped.

15. The femoral implant of claim 12, wherein the relief further includes a relief wall, the relief wall being inwardly tapered to reduce a profile size of the augment.

16. The femoral implant of claim 12, wherein the relief has a proximal end portion and a distal end portion, and wherein the proximal end portion is wider than the distal end portion.

17. The femoral implant of claim 12, wherein the relief is formed in the posterior side of the augment wall.

18. The femoral implant of claim 12, wherein the relief terminates midway between the proximal most end and the distal most end.

19. The femoral implant of claim 12, further comprising a pair of openings extending proximally from the distal most end, wherein the pair of openings is configured to receive placement of a pair of keels extending from the articular component.

20. The femoral implant of claim 12, wherein the anterior side extends at a first angle relative to the longitudinal axis, wherein the posterior side extends at a second angle relative to the longitudinal axis, and wherein the first angle is different from the second angle.

21. The femoral implant of claim 12, further comprising a second relief formed in the augment wall and extending through the augment wall from the outer portion to the inner portion, the second relief extending from the distal most end toward the proximal most end and along a second relief axis, wherein the second relief axis is oblique to the longitudinal axis and extends away from the longitudinal axis in a distal-to-proximal direction.

22. The femoral implant of claim 12, wherein the second relief terminates midway between the distal most end and the proximal most end.

* * * * *